United States Patent [19]

Giraldi et al.

[11] 4,010,274
[45] Mar. 1, 1977

[54] ISOINDOLINE DERIVATIVES HAVING PLATELET ANTI-AGGREGATING ACTIVITY

[75] Inventors: Pier Nicola Giraldi; Giuliano Nannini, both of Milan; Giovanni Riasoli, Vanese; Anna Spelta, Milan; Aurelio Contone, Como, all of Italy

[73] Assignee: Carlo Erba, Milan, Italy

[22] Filed: Oct. 16, 1975

[21] Appl. No.: 622,828

Related U.S. Application Data

[63] Continuation of Ser. No. 537,429, Dec. 30, 1974, abandoned, which is a continuation of Ser. No. 483,780, June 26, 1974, abandoned.

[30] Foreign Application Priority Data

July 27, 1973 Italy .................................. 27151/73

[52] U.S. Cl. .............................................. 424/274
[51] Int. Cl.$^2$ ........................................ A61K 31/40
[58] Field of Search .............. 424/274; 260/325 PH

[56] References Cited
UNITED STATES PATENTS 3,767,805   10/1973   Carney et al. ...................... 424/274

Primary Examiner—Norman A. Drezin
Attorney, Agent, or Firm—Dennis P. Clarke

[57] ABSTRACT

Composition and method for the prevention and treatment of syndromes caused by platelet-aggregation disorders wherein the active ingredient is a compound of the formula:

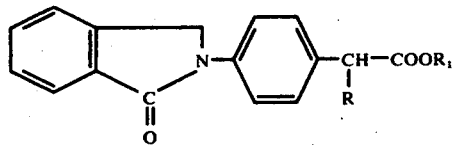

wherein R is H or $C_1$–$C_4$ alkyl and $R_1$ is H, $C_1$–$C_4$ alkyl or

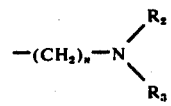

wherein $n$ is 1 or 2, and $R_2$ and $R_3$ are H or $C_1$–$C_4$ alkyl, or salts thereof.

6 Claims, No Drawings

ISOINDOLINE DERIVATIVES HAVING PLATELET ANTI-AGGREGATING ACTIVITY

This is a continuation, of application Ser. No. 537,429 filed Dec. 30, 1974 now abandoned, which is a continuation of Ser. No. 483,780, filed June 26, 1974 now abandoned.

The present invention relates to a method for the prevention and treatment of syndromes caused by platelet-aggregation disorders, and to pharmaceutical compositions useful to this purpose.

British patent No. 1,344,663 and pending U.S. Pat. application Ser. No. 426,554, filed Dec. 20, 1973, which is a continuation application of U.S. Pat. application Ser. No. 194,500, filed Nov. 1, 1971 now abandoned, describe compounds provided with anti-inflammatory activity having the following general formula:

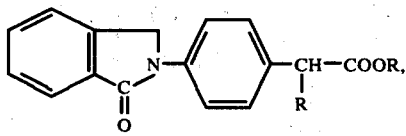

wherein R may be a hydrogen atom or $C_1$–$C_4$ alkyl, $R_1$ may be a hydrogen atom, $C_1$–$C_4$ alkyl or a group of the following formula:

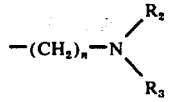

wherein $n$ may be 1 or 2, and each of $R_2$ and $R_3$ groups, being the same or different, may be hydrogen or $C_1$–$C_4$ alkyl, and the salts of the compounds of formula (I), wherein $R_1$ is hydrogen, with physiologically acceptable bases, as well as the salts of the compounds of formula (I), wherein $R_1$ is the

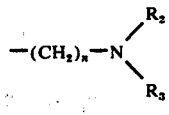

group, with physiologically acceptable acids. In particular, said British patent and U.S. applications specifically describe at least one of the following compounds:

1-oxo-2-[p-(carboxymethyl)-phenyl]-isoindoline and its ester with 2-(dimethylamino) ethanol and its salt with 2-(dimethylamino) ethanol;

1-oxo-2-{p-[(α-methyl)-carboxymethyl]-phenyl}-isoindoline and its ester with 2-(dimethylamino) ethanol and its salt with 2-(dimethylamino)ethanol;

1-oxo-2-{p-[(α-ethyl)-carboxymethyl]-phenyl}-isoindoline and its ester with 2-(dimethylamino) ethanol and its salt with 2-(dimethylamino) ethanol;

1-oxo-2-{p-[(α-propyl)-carboxymethyl]-phenyl}-isoindoline and its ester with 2-(dimethylamino) ethanol and its salt with 2-(dimethylamino) ethanol;

1-oxo-2-{p-[(α-butyl)-carboxymethyl]-phenyl}-isoindoline and its ester with 2-(dimethylamino) ethanol and its salt with 2-(dimethylamino) ethanol;

1-oxo-2-{p-[(α-methyl)-carbethoxymethyl]-phenyl}-isoindoline.

The compounds of formula (I) may be prepared as described in the above-cited British patent, by reacting a compound of formula

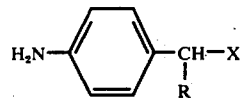

wherein X is carbalkoxy or a cyano group and R is as hereabove defined, with o-cyano-benzyl-bromide or with phthalide or thiophthalide or with phthalic aldehyde or phthalic anhydride or with a phthalic acid diester.

The optional salification as well as hydrolysis or reduction reactions which may be eventually necessary, can be performed by using conventional methods.

The details inherent to the methods of preparation are described in the above-identified British patent and in the above-identified U.S. applications, the disclosures of which are incorporated herein by reference.

Surprisingly, we have now found that the compounds of formula (I) and their salts are also provided with a high platelet-antiaggregating activity, and are therefore useful in the prevention and treatment of syndromes caused by platelet-aggregation disorders, such as, for example, thrombosis or, pulmonary embolism, (see for instance Canadian Med. Assoc. J. 108:443–465, 1973.)

The anti-aggregating activity of the compounds of the present invention is obtained at extremely low dosages if compared with compounds of different chemical structure having analogous activity. Said activity was tested "in vitro" and "in vivo" both in animals and humans by using G.C.R. Born's technique, Nature (London) 194: 927–929, 1962.

The compounds 1-oxo-2-{p-[(α-methyl)-carboxymethyl]-phenyl}-isoindoline, 1-oxo-2-{p-[(α-ethyl)-carboxymethyl]-phenyl}-isoindoline and 1-oxo-2-{p-[(α-butyl)-carboxymethyl]-phenyl}-isoindoline have proved to be particularly active, and the data herebelow reported refer to said compounds.

The lowest dose inhibiting the release reaction caused by ADP in the in vitro test is as follows:

| | |
|---|---|
| 1-oxo-2-{p-[(α-methyl)-carboxymethyl]-phenyl}-isoindoline | μM/ml of plasma 4.6 γ/ml of plasma 1.3 |
| 1-oxo-2-{p-[(α-ethyl)-carboxymethyl]-phenyl}-isoindoline | μM/ml of plasma 4.6 γ/ml of plasma 1.3 |
| 1-oxo-2-{p-[(α-butyl)-carboxymethyl]-phenyl}-isoindoline | μM/ml of plasma 4.6 γ/ml of plasma 1.5 |

The lowest dose able to inhibit the release reaction caused by ADP in the blood drawn 15 minutes after the intravenous administration to guinea-pigs is as follows:

| | | |
|---|---|---|
| 1-oxo-2-{p-[(α-methyl)-carboxymethyl]-phenyl}--isoindoline | μM/kg | 460 mg/kg 0.13 |
| 1-oxo-2-{p-[(α-ethyl)-carboxymethyl]-phenyl}--isoindoline | μM/kg | 460 mg/kg 0.13 |
| 1-oxo-2-{p-[(α-butyl)-carboxymethyl]-phenyl}-isoindoline | μM/kg | 460 mg/kg 0.15. |

The tests performed in order to determine the duration time of the pharmacological activity of the respective compounds have shown that 1-oxo-2-{p-[(α-ethyl)-carboxymethyl]-phenyl}-isoindoline is provided with the longest activity.

Guinea-pigs were orally given 1-oxo-2-{p-[(α-ethyl)-carboxymethyl]-phenyl}-isoindoline suspended in methyl cellulose at a dosage of 1.2 mg/kg. Then the blood of the animals treated was drawn after different intervals of time, and the anti-aggregating activity, evaluated as action inhibiting the release reaction caused by ADP, was studied.

The peak of the activity already observable 15 minutes after the administration of the compound lasted up to the second hour, then gradually fell down to 44% of the peak of the activity, this value still persisting 12 hours after the administration of the compound.

The compounds of the invention were also submitted to experiments in clinical pharmacology. The data herebelow reported refer to 1-oxo-2-{p-[(α-ethyl)-carboxymethyl]-phenyl}-isoindoline, which has proved to be the compound provided with the highest anti-aggregating activity. Said compound was administered per os to ten healthy human volunteers at a single daily dose of 100 mg. The action on platelet-aggregation was determined by means of in vitro tests performed on plasma full of platelets drawn from the tested volunteers before the administration of the compound and 2, 4, 24 hours afterwards. The anti-aggregating activity was evaluated by using the abovecited Born's nephelometric technique. The aggregation was induced both by ADP and Trombofax. The analysis was performed by calculating the percentage of platelet-aggregation after 90 inches, 180 inches, and 360 inches.

It was found that 1-oxo-2-{p-[(α-ethyl)-carboxymethyl]-phenyl}-isoindoline shows the peak of its action inhibiting platelet-aggregation in humans around the second and fourth hour, the action still persisting in any event 24 hours after the administration of the compound, thereby rendering it useful in the prevention and treatment of syndromes deriving from platelet-aggregation disorders, such as, for instances, the conditions hereabove specified.

The compounds of the invention can be administered by using the conventional therapeutical formulations. They are preferably administered orally.

Preferred pharmaceutical compositions are therefore tablets, capsules, pills, and the like, where the active principle is mixed with conventional solid excipients, such as, for instance, talc, starch, stearic acid, magnesium stearate, cellulose, and the like.

Daily doses suitable for the oral administration to humans may range in adults between approximately 50 mg and approximately 200 mg. Preferably 1 to 4 tablets containing 50 mg of active principle may be daily administered.

We claim:

1. A method for the prevention and treatment of platelet aggregation comprising administering to a patient in need thereof of a therapeutically effective amount of a compound of the formula:

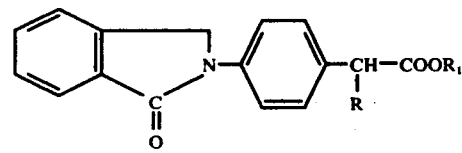

wherein R is hydrogen or alkyl of 1–4 carbon atoms, $R_1$ is hydrogen, alkyl of 1–4 carbon atoms or a group of the formula:

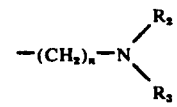

wherein $n$ may be 1 or 2 and each of $R_2$ and $R_3$, being the same or different, are hydrogen or alkyl of 1–4 carbon atoms or a salt of the compound wherein $R_1$ is hydrogen with a physiologically acceptable base or a salt of the compound wherein $R_1$ is

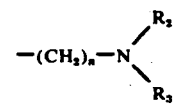

with a physiologically acceptable acid.

2. A method according to claim 1 where said compound is 1-oxo-2-{p-[(α-methyl)-carboxymethyl]-phenyl}-isoindoline.

3. A method according to claim 1, where said compound is 1-oxo-2-{p-[(α-ethyl)-carboxymethyl]-phenyl}-isoindoline.

4. A method according to claim 1, where said compound is 1-oxo-2-{p-[(α-butyl)-carboxymethyl]-phenyl}-isoindoline.

5. A method according to claim 1, where said compound is orally administered.

6. A method according to claim 1, wherein from 50 to 200 mg of said compound is administered daily to an adult human.

* * * * *